United States Patent
Hara et al.

(12)

(10) Patent No.: US 6,369,240 B1
(45) Date of Patent: Apr. 9, 2002

(54) GAS-PHASE OXIDIZATION PROCESS AND PROCESS FOR THE PREPARATION OF PHTHALIC ANHYDRIDE

(75) Inventors: Tadanori Hara; Nobuyoshi Nakamura, both of Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/297,019

(22) PCT Filed: Oct. 22, 1997

(86) PCT No.: PCT/JP97/03823

§ 371 Date: Apr. 23, 1999

§ 102(e) Date: Apr. 23, 1999

(87) PCT Pub. No.: WO98/17608

PCT Pub. Date: Apr. 30, 1998

(30) Foreign Application Priority Data

Oct. 23, 1996 (JP) ............................................. 8-280625
Oct. 23, 1996 (JP) ............................................. 8-280626

(51) Int. Cl.$^7$ ........................................... C07D 307/89
(52) U.S. Cl. ....................................... 549/249; 549/248
(58) Field of Search ................................. 549/248, 249

(56) References Cited

U.S. PATENT DOCUMENTS 4,582,912 A * 4/1986 Saleh et al. .................. 549/248
5,229,527 A * 7/1993 Ueda et al. .................. 549/248
5,235,071 A * 8/1993 Ueda et al. .................. 549/248

FOREIGN PATENT DOCUMENTS

| EP | 0286448 | 10/1988 | .................. 549/248 |
| JP | 4424580 | 10/1969 | .................. 549/248 |
| JP | 4613255 | 4/1971 | .................. 549/248 |
| JP | 49 34672 | 9/1974 | .................. 549/248 |
| JP | 5857374 A | 4/1983 | .................. 549/248 |
| JP | 58 57374 | 4/1983 | .................. 549/248 |
| JP | 63253080 A | 10/1988 | .................. 549/248 |

* cited by examiner

Primary Examiner—Alan L. Rotman
Assistant Examiner—Raymond Covington
(74) Attorney, Agent, or Firm—Birch, Stewart, Kolasch & Birch, LLP

(57) ABSTRACT

This invention relates to the vapor-phase oxidation of hydrocarbons by passing a gaseous mixture comprising of a molecular oxygen-containing gas and hydrocarbons which may contain substituents to a fixed bed of catalyst and provides a process for vapor-phase oxidation to be effected by passing a gaseous mixture of raw materials to a fixed bed of catalyst in which the void ratio of the catalyst layers increases by stages in one step or more from upstream downward in the flow of the gaseous mixture of raw materials. For example, the process can oxidize in vapor phase such hydrocarbons as naphthalene, xylene, benzene, toluene, durene, butene, acenaphthene, anthracene, indene and their derivatives in high yields with high productivity. Moreover, the process can prepare phthalic anhydride in high yields with high productivity by the vapor-phase oxidation of naphthalene or ortho-xylene.

14 Claims, No Drawings

GAS-PHASE OXIDIZATION PROCESS AND PROCESS FOR THE PREPARATION OF PHTHALIC ANHYDRIDE

This application is the national phase under 35 U.S.C. §371 of PCT International Application No. PCT/JP97/03823 which has an International filing date of Oct. 22, 1997 which designated the United States of America.

FIELD OF TECHNOLOGY

This invention relates to a process for the vapor-phase oxidation of hydrocarbons such as naphthalene, xylene, benzene, toluene, durene, butene, anthracene, indene and their derivatives. This invention also relates to a process for preparing phthalic anhydride by the oxidation of naphthalene or xylene.

BACKGROUND TECHNOLOGY

It is known that the catalytic vapor-phase oxidation of naphthalene, ortho-xylene, indene and the like gives phthalic anhydride and, likewise, the process yields maleic anhydride from benzene or butene, benzoic acid from toluene, pyromellitic dianhydride from durene and phthalic anhydride or anthraquinone from anthracene.

The aforementioned process for the catalytic vapor-phase oxidation generates a large amount of heat in the reaction and a practice generally adopted for heat removal is to fill a reactor tube of relatively small diameter with a catalyst to form a fixed bed of catalyst and pass a gaseous mixture of a raw material and a molecular oxygen-containing gas such as air to the catalyst bed [Japan Tokkyo Koho Nos. Sho 44-24580 (1969) and Sho 46-13255 (1971)].

Catalysts useful for the process normally consist of active components, indispensable members of which are titanium oxide and vanadium pentoxide, deposited on inert carriers. A process is also known which utilizes two kinds of catalysts differing from each other in catalytic activity. For example, the specification of EP286448 discloses the following process for preparing phthalic anhydride. A catalyst bed is constructed of a layer of a first catalyst made by depositing catalytically active components containing 90 to 67% by weight of titanium dioxide, 8 to 30% by weight of vanadium pentoxide and 2 to 5% by weight of a compound of cesium (calculated as sulfate) and showing a specific surface area of 20 $m^2/g$ or more on a nonporous inert carrier and a layer of a second catalyst made by depositing catalytically active components containing no more than 0.1% by weight of a compound of alkali metal (calculated as sulfate), 94 to 67% by weight of titanium dioxide and 5 to 30% by weight of vanadium pentoxide on a nonporous inert carrier, with the first catalyst placed upstream and the second catalyst downstream in the flow of the gaseous mixture of raw materials. A gaseous mixture of naphthalene or ortho-xylene and a molecular oxygen-containing gas is then brought into contact with the catalyst bed to be oxidized to phthalic anhydride.

This process advantageously gives the intended product such as phthalic anhydride in high yields; still there is a strong demand for improvement of the productivity per unit catalyst volume.

The productivity can be increased by increasing the yield and also by increasing the flow rate of a gaseous mixture of a raw material and a molecular oxygen-containing gas, that is, by increasing GHSV, or by increasing the concentration of raw material in the gaseous mixture. There is, however, a theoretical limit to the increasing of the yield and it is difficult to look for a significant improvement here. There is also a limit to the increasing of GHSV as it increases the cost of motive power to drive air blowers. On the other hand, increasing the concentration of raw material creates problems such as readier occurrence of incomplete reaction accompanied by increased formation of by-products, execution of the reaction in the explosive range of raw material and generation of more heat per unit volume with easier formation of the so-called hot spots, but it offers an advantage of reducing the cost of equipment and utilities.

It is an object of this invention to provide a process for vapor-phase oxidation which is capable of giving the intended product not only in high yields but also with high productivity. In case phthalic anhydride is the intended product, it is an object of this invention to provide a process for preparing phthalic anhydride not only in high yields but also with high productivity.

DISCLOSURE OF THE INVENTION

Firstly, in executing the oxidation of hydrocarbons by passing a gaseous mixture comprising of a molecular oxygen-containing gas and hydrocarbons which may contain substituents to a fixed bed of catalyst, this invention relates to a process for vapor-phase oxidation which is characterized by passing said gaseous mixture to a fixed bed of catalyst which increases by stages in void ratio in one step or more from upstream downward in the flow of said gaseous mixture. In this case, the void ratio of a catalyst layer placed most upstream or $V_1$ and the void ratio of a catalyst layer placed most downstream or $V_2$ preferably satisfy the relationship $V_1/V_2=0.6~0.9$. Moreover, in construction of the catalyst bed, a given catalyst is preferably so arranged in layers that the oxidative activity increases by stages in one step or more from upstream downward.

Secondly, in preparing phthalic anhydride by passing a gaseous mixture comprising of a molecular oxygen-containing gas and naphthalene and/or ortho-xylene to a fixed bed of catalyst, this invention relates to a process for preparing phthalic anhydride which is characterized by utilizing a catalyst containing titanium dioxide and vanadium pentoxide as principal catalytically active components and also by passing said gaseous mixture to a fixed bed of catalyst which increases by stages in void ratio in one step or more from upstream downward in the flow of said gaseous mixture.

Thirdly, this invention relates to a process for preparing phthalic anhydride wherein the aforementioned catalyst comprises a catalyst placed upstream and a catalyst placed downstream in the flow of the gaseous mixture of raw materials; the aforementioned upstream catalyst is made by depositing catalytically active components containing 75 to 90% by weight of titanium dioxide, 10 to 20% by weight of vanadium pentoxide, 1.0 to 3.5% by weight of a compound of cesium (calculated as sulfate) and 0.1 to 1.8% by weight of a compound of at least one metal selected from barium, magnesium, yttrium, lanthanum and cerium (calculated as oxide of selected metal) and showing a specific surface area of 100 to 160 $m^2/g$ on a nonporous inert carrier while the aforementioned downstream catalyst is made by depositing catalytically active components containing less than 0.1% by weight of a compound of alkali metal (calculated as sulfate), 75 to 90% by weight of titanium dioxide, 10 to 20% by weight of vanadium pentoxide, 1.0 to 3.0% by weight of a compound of phosphorus (calculated as oxide) and 0.3 to 2.0% by weight of a compound of at least one metal selected from tungsten, molybdenum, tin, antimony and bismuth (calculated as oxide of selected metal) and showing a specific surface area of 70 to 100 m²/g on a nonporous inert carrier. The upstream catalyst may contain two kinds or more of catalysts and, if such is the case, the amount of cesium preferably decreases by stages from upstream downward within the aforementioned range.

Raw material hydrocarbons with or without substituents may be any hydrocarbons as long as they are oxidized in vapor phase to yield the intended and they include benzene, alkylbenzenes, naphthalene, alkylnaphthalenes, anthracene, indene, butene and alkylpyridines with or without substituents such as halogen, hydroxyl and carboxyl.

The category of oxidation reaction includes ordinary oxidation in which oxygen increases, oxidative dehydrogenation in which hydrogen decreases and ammoxidation in which other reactions take place together with oxidation. Examples of the intended products are acid anhydrides such as phthalic anhydride, maleic anhydride and pyromellitic dianhydride, carboxylic acids such as benzoic acid and a compound such as styrene to be obtained from ethylbenzene. The process of this invention is best suited for a reaction which is primarily directed for the preparation of carboxylic acids or acid anhydrides where the heat of reaction is relatively high and the reaction is carried out on a large scale. In particular, the process is suited for a reaction which is intended for the preparation of phthalic anhydride. The raw material hydrocarbon useful here is naphthalene or ortho-xylene or a mixture of the two.

The vapor-phase oxidation of this invention is effected by passing a gaseous mixture of the aforementioned hydrocarbons and a molecular oxygen-containing gas such as air to a fixed bed of catalyst. The fixed bed of catalyst is exemplified by a reactor tube filled with a catalyst and af catalyst is exemplified by a reactor tube filled with a catalyst and a reactor tube with a diameter of 10 to 100 mm, preferably 20 to 40 mm, is desirable for heat removal. It is advantageous to use a shell-and-tube reactor in which a large number of catalyst-filled reactor tubes are arranged and surrounded by a heat transfer medium.

The fixed bed of catalyst to be used in this invention increases by stages in void ratio in one step or more, namely in two layers or more of catalysts, preferably in two steps or more, namely in three layers of more of catalysts, from upstream downward in the flow of the gaseous mixture of raw materials. The void ratio here is calculated as follows:

$$\text{Void ratio}(V\%)=[(B)/(A)]\times 100$$

wherein A is the volume in cc of a reactor tube or a measuring cylinder of the same diameter as the reactor tube filled with a given catalyst to a specified position or graduation and B is the volume in cc of ethanol added to the catalyst-filled reactor tube or measuring cylinder to the aforementioned position or graduation.

The void ratio of the catalyst layer can be controlled by changing the shape or size of the catalyst. For example, the void ratio can be changed widely by making the catalyst in the shape of a sphere, a cylinder or a ring. Even where the catalyst is shaped like a ring, a common Raschig ring gives a void ratio different from that of a Raschig ring modified by providing projections inside or outside of the ring and, moreover, a Raschig ring itself can be changed in void ratio by changing the wall thickness of the ring. Execution of a vapor-phase oxidation with higher productivity necessitates an increase in GHSV. Since a smaller void ratio causes a greater pressure loss, it is advisable to control the void ratio at 40% or more, preferably 50% or more. Suitable for this purpose is a ring containing cavities inside or a ring modified further by providing projections and partitions.

The void ratio of catalyst layers is changed in one step or more. However, a random increase in the number of kind of catalyst merely complicates preparation and filling of the catalysts and it is advisable to effect the change at most in 2 to 3 steps, namely in 3 to 4 layers, more preferably 3 layers. The difference in void ratio between the adjacent catalyst layers is held at 3% or more, preferably 5 to 25%, more preferably 8 to 16%, and the void ratio of the catalyst layer placed most upstream or $V_1$ and that of the catalyst layer placed most downstream or $V_2$ are so adjusted that they satisfy the relationship $V_1/V_2=0.6\sim0.9$, preferably $V_1/V_2=0.7\sim0.8$. The difference between $V_2$ and $V_1$ is held on the order of 5 to 30%, preferably 10 to 25%.

Catalysts in common use are composed of catalytically active components deposited on carriers. The process of this invention can be practiced effectively by changing the void ratio alone, but it is still more desirable to change the catalytically active components in such a manner as to cause the oxidative activity increase toward downstream. The oxidative activity is related to the reaction rate and its magnitude can be judged by measuring the optimum reaction temperature. It is generally known that the activity of titanium dioxide/vanadium pentoxide-based catalysts which are commonly used for vapor-phase oxidation is decreased by the compounds of metals of Groups I a and II a such as alkali metals and alkaline earth metals and increased by many of the compounds of phosphorus and of metals of Groups IV to VIII such as tin. Therefore, it is possible to change the activity by adding these compounds in varying amounts. Furthermore, the activity changes with the specific surface area of catalyst or with the amount of vanadium pentoxide and increasing the specific surface area or the amount of vanadium pentoxide helps to increase the activity.

In case the process is intended for the preparation of phthalic anhydride, catalysts containing titanium dioxide and vanadium pentoxide as principal active components are used and it is desirable to change the activity by adding a compound of alkali metal to the upstream catalyst and compounds of phosphorus and tin to the downstream catalyst.

Preferably, an upstream catalyst contains 65 to 95% by weight of titanium dioxide, 4 to 30% by weight of vanadium pentoxide and 0.1 to 5% by weight of a compound of alkali metal (calculated as sulfate) as catalytically active components and a downstream catalyst contains 65 to 95% by weight of titanium dioxide, 4 to 30% by weight of vanadium pentoxide and 0.1 to 5% by weight of phosphorus (calculated as oxide) as catalytically active components. In case the catalysts are placed in three layers or more, the catalyst in the intermediate layer has a composition somewhere between those of the aforementioned two.

More preferably, an upstream catalyst contains 75 to 90% by weight of titanium dioxide, 10 to 20% by weight of vanadium pentoxide, 1.0 to 3.5% by weight of a compound of cesium (calculated as sulfate) and 0.1 to 1.8% by weight of a compound of at least one metal selected from barium, magnesium, yttrium, lanthanum and cerium (calculated as oxide of selected metal) and shows a specific surface area of 100 to 160 m2/g. Here, the catalyst is so arranged that the amounts of the compound of cesium and the compound of a metal selected from barium, magnesium, yttrium, lanthanum and cerium increase toward upstream and the specific surface area decreases toward upstream. Moreover, the catalyst desirably contains no more than 0.1% by weight of the sum total of a compound of phosphorus and a compound of at least one metal selected from tungsten, molybdenum, tin, antimony and bismuth (calculated as oxide).

Application of two kinds or more of catalyst layers as an upstream catalyst with staged decrease of the compound of cesium from upstream downward within the aforementioned range allows an expansion of the area in which the oxidation reaction takes place with vigorous generation of heat and also a smooth change in temperature in the upstream catalyst. The number of kinds of catalyst layer in the upstream catalyst may be two or three or more, but two or three will be preferred in view of the time required for the preparation of catalysts and so forth.

In an upstream catalyst of this type, the catalyst layer to be placed most upstream is controlled to contain 1.5 to 3.5% by weight of a compound of cesium (calculated as sulfate) and 0.3 to 1.8% by weight of a compound of at least one metal selected from barium, magnesium, yttrium, lanthanum and cerium (calculated as oxide of selected metal) and have a specific surface area of 100 to 140 m$^2$/g and the catalyst layer to be placed most downstream is controlled to contain 1.0 to 2.0% by weight of a compound of cesium (calculated as sulfate) and 0.1 to 1.6% by weight of a compound of at least one metal selected from barium, magnesium, yttrium, lanthanum and cerium (calculated as oxide of selected metal) and have a specific surface area of 120 to 160 m$^2$/g. Preferably, the compound of cesium and the compound of at least one metal selected from barium, magnesium, yttrium, lanthanum and cerium are made to increase toward upstream and the specific surface area is made to decrease toward upstream. Consequently, where three kinds of catalyst layers are used in an upstream catalyst, the catalyst layer to be placed intermediately is controlled to show values intermediate between those of the most upstream and most downstream catalyst layers regarding the aforementioned metal compounds and specific surface area.

On the other hand, a downstream catalyst is preferably controlled to contain 75 to 90% by weight of titanium dioxide, 10 to 20% by weight of vanadium pentoxide, 1.0 to 3.0% by weight of a compound of phosphorus (calculated as oxide) and 0.1 to 1.8% by weight of a compound of at least one metal selected from tungsten, molybdenum, tin, antimony and bismuth (calculated as oxide of selected metal) and have a specific surface area of 100 to 160 m$^2$/g. Preferably, the compound of phosphorus and the compound of at least one metal selected from tungsten, molybdenum, tin, antimony and bismuth are made to increase toward downstream and the specific surface area is made to increase toward downstream.

A preferable downstream catalyst consists of catalytically active components deposited on a nonporous inert carrier, said active components containing less than 0.1% by weight of a compound of alkali metal (calculated as sulfate), 75 to 90% by weight of titanium dioxide, 10 to 20% by weight of vanadium pentoxide, 1.0 to 3.0% by weight of a compound of phosphorus and 0.3 to 2.0% by weight of compounds of one kind or more selected from tungsten, molybdenum, tin, antimony and bismuth and showing a specific surface area of 70 to 100 m$^2$/g. Of the aforementioned compounds of metals, those of tungsten are preferable. Moreover, it is desirable that the downstream catalyst does not contain 0.1% by weight or more of the compounds of metals selected from barium, magnesium, yttrium, lanthanum and cerium (calculated as oxide).

It is allowable to apply two kinds or more of catalysts to the downstream catalyst and, in such a case, the amount of the compound of phosphorus and the specific surface area preferably increase toward downstream. However, the matter is simplified by using one kind of catalyst in the downstream catalyst.

A method for the preparation of a catalyst of the aforementioned kind will be described for the case of an upstream catalyst intended for the preparation of phthalic anhydride and other catalysts can be prepared in a similar manner as this method.

The catalyst in question is prepared by dissolving vanadium pentoxide or a compound of vanadium which is convertible to vanadium pentoxide by heating in a molecular oxygen-containing gas, for example, ammonium vanadate and sulfate, formate, acetate or tartrate of vanadium in water or in a mixture of an organic solvent such as alcohol and water, adding a compound of cesium and compounds of one kind or two kinds or more of metals selected from barium, magnesium, yttrium, lanthanum and cerium to the resulting solution, mixing the solution with finely divided particles of titanium dioxide or titanium hydroxide, applying the resulting slurry to a carrier by adhesion or impregnation, and heating the carrier. Here, the amount of the catalytically active components is 20 to 200 g, preferably 40 to 150 g, per 1 l of the carrier. The specific surface area of the catalytically active components is controlled, for example, by proper selection of the raw material titanium dioxide.

Suitable compounds of cesium include cesium sulfate, cesium oxide, cesium carbonate, cesium acetate and cesium nitrate and cesium sulfate is preferable among them. These compounds, with the exception of sulfate, change into oxide in a molecular oxygen-containing gas at high temperatures. Cesium is presumably present in the catalyst as cesium sulfate, cesium oxide or cesium vanadate and the preferable form is a salt of sulfur oxyacid such as cesium sulfate and cesium pyrosulfate. Likewise, the same is true of the compounds of metals selected from barium, magnesium, yttrium, lanthanum and cerium.

Compounds of phosphorus useful as components of downstream catalysts for the preparation of phthalic anhydride include ammonium phosphate, phosphoric acid, phosphorous acid and phosphate esters while useful compounds of metals selected from tungsten, molybdenum, tin, antimony and bismuth include their salts, oxyacid salts such as tungstates and oxides.

The catalytically active components are named as in the specification of this invention solely for the convenience of calculation and, as is well known, vanadium is present, for example, in the form of VOx (x=1~2.5) or vanadate and cesium in the form of cesium sulfate or cesium pyrosulfate.

The source of titanium dioxide to be used in the preparation of the catalysts of this invention is titanium dioxide of anatase type and titanium dioxide hydrate. The specific surface area can be controlled by changing the conditions for the preparation of these compounds.

Examples of the nonporous inert carrier are sintered or fused silicates, steatite, porcelain, alumina and silicon carbide. The carrier is spherical, cylindrical or annular with an equivalent diameter of 3 to 12 mm, preferably 4 to 8 mm. The height of a cylindrical or annular carrier is 3 to 10 mm, preferably 4 to 8 mm. Changing the shape or size of the carrier changes the void ratio as described earlier and also controls the geometric surface area of the catalyst.

Thus, changing the shape or size of the carrier can control the geometric surface area of the catalyst and the void ratio of the catalyst layer. Where the carrier is annular, a variety of rings are conceivable such as Raschig rings, rings with partitions and projections inside and rings with projections outside. Properly selected rings can control the geometric surface area and the void ratio of the catalyst layer.

A Raschig ring is taken as a standard in this invention and it is preferable to use an annular carrier with a larger geometric surface area than that of the standard and to let the void ratio of the catalyst layer decrease toward upstream.

The volume ratio of the upstream catalyst to the downstream catalyst is 100 parts of the former to 30 to 300 parts, preferably 60 to 150 parts, of the latter. In case the upstream catalyst is made up of two kinds or more of catalysts, the volume ratio inside the upstream catalyst is 100 parts of the one placed most upstream to 50 to 200 parts, preferably 70 to 150 parts, of others. Catalytic oxidation is normally effected by filling a multi-tube reactor with the downstream catalyst as lower layer to a specified height and then with the upstream catalyst as upper layer and passing a gaseous mixture of naphthalene or ortho-xylene or both and a molecular oxygen-containing gas such as air through the reactor from the top downward.

The length of each catalyst layer is preferably such as to fall within the range of (m/n)×(0.5~2.0), preferably (m/n)×(0.7~1.5) wherein m is the total length of the catalyst layers and n is the number of the kind of catalyst.

The oxidation reaction temperature, although varying with the type of reaction, is 300 to 400° C. (as niter temperature), preferably 330 to 380° C., in the preparation of phthalic anhydride. The concentration of naphthalene or ortho-xylene or both, that is, the concentration of raw material in the gaseous mixture is 30 to 160 g/m$^3$-air, preferably 90 to 150 g/m$^3$-air, and the space velocity is 1,000 to 8,000 hr$^{-1}$, preferably 2,000 to 5,000 hr$^{-1}$.

The process of this invention has a potentiality of increasing the productivity markedly and, to realize this, the process is preferably practiced by supplying the raw materials at a concentration in the explosive range, that is, 90 g/m$^3$-air or more. It is important to keep the raw materials below their ignition temperature to prevent explosions. The process is capable of broadening the range in which the heat of reaction is generated and, in consequence, it is possible to prevent local heat generation (formation of hot spots) and control with ease the temperature so that even the maximum temperature does not exceed the ignition temperature of naphthalene or 584° C.

In the process of this invention, the reaction takes place in a broad range because of a greater linear velocity of the gaseous mixture of raw materials in the upstream catalyst layer where the raw materials are present in a high concentration and, as a result, hot spots form with difficulty. The linear velocity decreases in the downstream catalyst layer and this works to diminish as much as possible the unreacted raw materials and the intermediate products. Thus, the intended product of vapor-phase oxidation, for example, phthalic anhydride, can be obtained in high yields with little by-products.

PREFERRED EMBODIMENT OF THE INVENTION

This invention will be described in detail below with reference to the accompanying examples. The notation % in the following examples is percent by weight unless otherwise stated.

(A) Preparation of Upstream Catalyst A

Pulverized titanium dioxide (containing the anatase type), ammonium metavanadate, cesium sulfate and barium acetate were mixed with water and emulsified with sufficient stirring to give a slurry. Porcelain Lessing rings, 8 mm in diameter and 6 mm in height, as carrier were preheated in a rotary furnace at 200 to 250° C. and then sprayed, while in rotation, with the aforementioned slurry until 100 g of the catalytically active components was placed on 1 l of the carrier. The rings were then calcined in a stream of air at 550° C. for 6 hours to give Catalyst A.

(B) Preparation of Intermediate-layer Catalyst B

Pulverized titanium dioxide (containing the anatase type), ammonium metavanadate, cesium sulfate and barium acetate (or a compound of magnesium, yttrium, lanthanum or cerium) were mixed with water and emulsified with sufficient stirring to give a slurry. Porcelain Lessing rings, 8 mm in diameter and 6 mm in height, as carrier were preheated in a rotary furnace at 200 to 250° C. and then sprayed, while in rotation, with the aforementioned slurry until 100 g of the catalytically active components was placed on 1 l of the carrier. The rings were then calcined in a stream of air at 550° C. for 6 hours to give Catalyst B.

(C) Preparation of Downstream Catalyst C

Pulverized titanium dioxide (containing the anatase type), ammonium metavanadate, ammonium phosphate and ammonium tungstate (or a compound of molybdenum, manganese, tin, antimony or bismuth) were mixed with water and emulsified with sufficient stirring to give a slurry. Porcelain Lessing rings, 8 mm in diameter and 6 mm in height, as carrier were preheated in a rotary furnace at 200 to 250° C. and then sprayed, while in rotation, with the aforementioned slurry until 100 g of the catalytically active components was placed on 1 l of the carrier. The rings were then calcined in a stream of air at 550° C. for 6 hours to give Catalyst C.

The composition and properties of Catalysts A, B and C are shown in Tables 1 and 2. The specific surface area of the catalytically active components was controlled by changing the conditions for the preparation of titanium dioxide. The void ratio was controlled by changing the wall thickness of the Lessing rings. In Tables 1 and 2, M in MOx designates a metal element.

TABLE 1

| Catalyst | | $V_2O_5$ (%) | $Cs_2SO_4$ (%) | $P_2O_5$ (%) | $MO_X$ M (%) | | Specified surface area (m$^2$/g) | Void ratio (%) |
|---|---|---|---|---|---|---|---|---|
| A | a1 | 17 | 2.5 | 0 | Ba | 1.0 | 120 | 60 |
|   | a2 | 17 | 2.5 | 0 | Ba | 1.0 | 120 | 70 |
|   | a3 | 20 | 2.5 | 0 | Ba | 1.0 | 115 | 60 |
|   | a4 | 17 | 3.0 | 0 | Ba | 1.0 | 120 | 60 |
| B | b1 | 17 | 1.5 | 0 | Ba | 1.0 | 140 | 73 |
|   | b2 | 17 | 1.0 | 0 | Ba | 1.0 | 140 | 68 |
|   | b3 | 17 | 1.5 | 0 | Ba | 1.0 | 140 | 71 |
|   | b4 | 17 | 1.5 | 0 | Ba | 0.5 | 140 | 68 |
| C | c1 | 20 | 0 | 2.0 | W | 1.0 | 80 | 75 |
|   | c2 | 20 | 0 | 2.0 | W | 1.0 | 80 | 70 |
|   | c3 | 20 | 0 | 1.5 | W | 1.0 | 80 | 60 |
|   | c4 | 20 | 0 | 2.0 | Sb | 1.5 | 80 | 75 |

TABLE 2

| Catalyst | | $V_2O_5$ (%) | $Cs_2SO_4$ (%) | $P_2O_5$ (%) | $MO_X$ M (%) | | Specified surface area (m$^2$/g) | Void ratio (%) |
|---|---|---|---|---|---|---|---|---|
| A | 1 | 14 | 2.5 | 0 | Ba | 1.5 | 120 | 60 |
|   | 2 | 17 | 2.5 | 0 | Mg | 1.0 | 120 | 60 |
|   | 3 | 20 | 2.5 | 0 | Ba | 1.0 | 115 | 60 |
|   | 4 | 17 | 2.0 | 0 | Ba | 1.0 | 120 | 60 |
|   | 5 | 17 | 3.0 | 0 | Ba | 1.0 | 120 | 60 |
|   | 6 | 17 | 2.5 | 0 | Mg | 1.5 | 120 | 60 |
|   | 7 | 17 | 2.5 | 0 | Ba | 0.5 | 120 | 60 |
|   | 8 | 17 | 2.0 | 0 | Mg | 1.0 | 120 | 60 |
|   | 9 | 17 | 2.0 | 0 | Y | 1.0 | 120 | 60 |
|   | 10 | 17 | 2.0 | 0 | La | 1.0 | 120 | 60 |
|   | 11 | 17 | 2.0 | 0 | Ce | 1.0 | 120 | 60 |
|   | 12 | 14 | 2.5 | 0 | Ba | 1.5 | 120 | 60 |
|   | 13 | 17 | 2.5 | 0 | Mg | 1.0 | 120 | 70 |
|   | 14 | 17 | 2.5 | 0 | — | 0 | 120 | 60 |
|   | 15 | 17 | 4.5 | 0 | Ba | 1.0 | 120 | 60 |
|   | 16 | 17 | 0.5 | 0 | Ba | 1.0 | 120 | 60 |
|   | 17 | 17 | 2.5 | 0 | Ba | 2.5 | 120 | 60 |
|   | 18 | 17 | 2.5 | 0 | Ba | 1.0 | 90 | 60 |
| B | 1 | 17 | 1.0 | 0 | Ba | 1.0 | 140 | 68 |
|   | 2 | 17 | 2.0 | 0 | Ba | 1.0 | 140 | 68 |
|   | 3 | 17 | 1.5 | 0 | Ba | 1.0 | 140 | 68 |
|   | 4 | 17 | 1.0 | 0 | Mg | 1.5 | 140 | 68 |
|   | 5 | 17 | 1.5 | 0 | Ba | 0.5 | 140 | 68 |
|   | 6 | 14 | 2.0 | 0 | Mg | 1.0 | 140 | 68 |
|   | 7 | 20 | 1.5 | 0 | Ba | 1.0 | 140 | 68 |
|   | 8 | 17 | 1.5 | 0 | Mg | 1.0 | 140 | 68 |
|   | 9 | 17 | 1.5 | 0 | Y | 1.0 | 140 | 68 |
|   | 10 | 17 | 1.5 | 0 | La | 1.0 | 140 | 68 |
|   | 11 | 17 | 1.5 | 0 | Ce | 1.0 | 140 | 68 |
|   | 12 | 17 | 1.0 | 0 | Ba | 1.0 | 140 | 60 |
|   | 13 | 17 | 1.0 | 0 | Ba | 1.0 | 140 | 70 |
|   | 14 | 17 | 1.5 | 0 | — | 0 | 140 | 68 |
|   | 15 | 17 | 1.5 | 0 | — | 0 | 100 | 68 |

TABLE 2-continued

| Catalyst | | V$_2$O$_5$ (%) | Cs$_2$SO$_4$ (%) | P$_2$O$_5$ (%) | MO$_X$ M | (%) | Specified surface area (m$^2$/g) | Void ratio (%) |
|---|---|---|---|---|---|---|---|---|
| C | 1 | 20 | 0 | 2.0 | W | 1.0 | 80 | 75 |
|   | 2 | 20 | 0 | 2.5 | W | 1.0 | 80 | 75 |
|   | 3 | 20 | 0 | 1.5 | W | 1.0 | 80 | 75 |
|   | 4 | 20 | 0 | 2.0 | Sb | 1.0 | 80 | 75 |
|   | 5 | 20 | 0 | 2.0 | W | 1.0 | 80 | 75 |
|   | 6 | 15 | 0 | 2.0 | Sn | 1.0 | 80 | 75 |
|   | 7 | 25 | 0 | 2.0 | W | 1.0 | 80 | 75 |
|   | 8 | 20 | 0 | 2.0 | Mo | 1.0 | 80 | 75 |
|   | 9 | 20 | 0 | 2.0 | Sn | 1.0 | 80 | 75 |
|   | 10 | 20 | 0 | 2.0 | Sb | 1.0 | 80 | 75 |
|   | 11 | 20 | 0 | 2.0 | Bi | 1.0 | 80 | 75 |
|   | 12 | 20 | 0 | 2.0 | W | 1.0 | 80 | 60 |
|   | 13 | 15 | 0 | 2.0 | Sn | 1.0 | 80 | 70 |
|   | 14 | 20 | 0 | 2.0 | — | 0 | 80 | 75 |
|   | 15 | 20 | 0 | 2.0 | W | 1.0 | 40 | 75 |

EXAMPLE 1

A reactor tube with an inside diameter of 25 mm was immersed in a niter bath controlled at an optimum temperature (340 to 360° C.) and filled with the catalysts shown in Table 1 in the order of Catalyst C, Catalyst B and Catalyst A from the bottom upward and a gaseous mixture of naphthalene or ortho-xylene and air was passed from the top of the reactor tube. The reaction conditions and the results are shown in Tables 3 and 4.

Comparative Example 1

The reaction was carried out by using the catalysts shown in Table 1 under the conditions shown in Table 4. The results are shown in Table 4.

As for the terminology used in Tables 3 and 4, the terms catalyst and parenthesized length of layer respectively indicate the kind of catalyst used and the length of layer of each catalyst in the order of the upstream, intermediate and downstream catalysts. In the raw material column, N refers to naphthalene, X to ortho-xylene and N/X to a 1:1 mixture of naphthalene and ortho-xylene. The amount supplied designates the amount in gram of the raw materials supplied in one hour to the catalyst layer and the concentration designates the amount in gram of the raw materials in 1 Nm$^3$ of air. In the yield column, PA refers to phthalic anhydride, NQ to naphthoquinone and PL to phthalide. The term "hot spot" means impossibility of continuation of reactions due to an excessive rise of temperature in the hot spot area.

TABLE 3

| Experiment No. | Catalyst (Length of layer: cm) | Raw material | Amount supplied g/hr | Concentration g/m$^3$ | Yield PA wt % | NQ wt % | PL wt % |
|---|---|---|---|---|---|---|---|
| 1 | a1(80) -b1(80) -c1(120) | N | 300 | 140 | 106.2 | tr | — |
|   |   |   | 320 | 107 | 106.0 | 0.05 | — |
|   |   |   | 340 | 113 | 106.5 | 0.06 | — |
|   |   |   | 360 | 120 | 106.5 | 0.08 | — |
|   |   |   | 360 | 130 | 106.6 | 0.42 | — |
|   |   |   | 370 | 140 | 106.5 | 0.13 | — |
|   |   | X | 300 | 101 | 115.5 | — | 0.01 |
|   |   |   | 340 | 115 | 115.3 | — | 0.05 |
|   |   |   | 360 | 121 | 116.1 | — | 0.07 |
|   |   |   | 360 | 130 | 116.0 | — | 0.09 |
|   |   |   | 370 | 140 | 115.9 | — | 0.10 |
|   |   | N/X | 300 | 100 | 110.5 | 0.02 | 0.01 |
|   |   |   | 320 | 108 | 111.2 | 0.03 | 0.03 |
|   |   |   | 340 | 115 | 111.3 | 0.04 | 0.05 |
|   |   |   | 360 | 121 | 111.3 | 0.05 | 0.07 |
| 2 | a1(80) -b2(80) -c1(120) | N | 300 | 101 | 105.9 | tr | — |
|   |   |   | 320 | 107 | 106.2 | 0.11 | — |
|   |   |   | 340 | 115 | 106.1 | 0.10 | — |
|   |   |   | 360 | 120 | 106.3 | 0.13 | — |
|   |   |   | 360 | 130 | 106.2 | 0.15 | — |
|   |   |   | 370 | 140 | 106.1 | 0.17 | — |
|   |   | X | 300 | 100 | 115.0 | — | 0.05 |
|   |   |   | 340 | 115 | 115.1 | — | 0.07 |
|   |   |   | 360 | 120 | 115.3 | — | 0.10 |
|   |   |   | 360 | 130 | 115.4 | — | 0.11 |
|   |   |   | 370 | 140 | 115.3 | — | 0.11 |
|   |   | N/X | 300 | 100 | 110.1 | 0.04 | 0.03 |
|   |   |   | 320 | 108 | 110.6 | 0.06 | 0.05 |
|   |   |   | 340 | 115 | 111.0 | 0.09 | 0.09 |
|   |   |   | 360 | 120 | 111.1 | 0.10 | 0.10 |
| 3 | a1(80) -b2(80) -c2(120) | N | 300 | 102 | 106.4 | 0.13 | — |
|   |   |   | 320 | 107 | 106.5 | 0.15 | — |
|   |   |   | 340 | 115 | 106.5 | 0.16 | — |
|   |   |   | 360 | 121 | 106.7 | 0.18 | — |
|   |   |   | 360 | 130 | 106.9 | 0.10 | — |
|   |   |   | 370 | 140 | 106.8 | 0.11 | — |
|   |   | X | 300 | 101 | 115.0 | — | 0.06 |
|   |   |   | 340 | 115 | 115.2 | — | 0.08 |
|   |   |   | 360 | 121 | 116.1 | — | 0.10 |
|   |   |   | 360 | 130 | 116.0 | — | 0.09 |
|   |   |   | 370 | 141 | 116.1 | — | 0.11 |
|   |   | N/X | 300 | 101 | 110.2 | 0.12 | 0.04 |
|   |   |   | 320 | 108 | 110.3 | 0.13 | 0.05 |
|   |   |   | 340 | 115 | 111.9 | 0.16 | 0.08 |
|   |   |   | 360 | 121 | 111.1 | 0.17 | 0.10 |

TABLE 4

| Experiment No. | Catalyst (Length of layer: cm) | Raw material | Amount supplied g/hr | Concentration g/m$^3$ | Yield PA wt % | NQ wt % | PL wt % |
|---|---|---|---|---|---|---|---|
| 4 | a2(80) -b1(80) -c1(120) | N | 300 | 101 | 106.2 | 0.07 | — |
|   |   |   | 320 | 107 | 106.5 | 0.10 | — |
|   |   |   | 340 | 114 | 106.4 | 0.12 | — |
|   |   |   | 360 | 121 | 106.7 | 0.14 | — |
|   |   |   | 360 | 130 | 106.5 | 0.10 | — |
|   |   | X | 300 | 100 | 115.3 | — | 0.04 |
|   |   |   | 340 | 115 | 115.5 | — | 0.05 |
|   |   |   | 360 | 120 | 116.1 | — | 0.08 |

TABLE 4-continued

| Experi-ment No. | Catalyst (Length of layer: cm) | Raw material | Amount supplied g/hr | Concentration g/m³ | Yield PA wt % | NQ wt % | PL wt % |
|---|---|---|---|---|---|---|---|
|  |  |  | 360 | 130 | 116.0 | — | 0.10 |
|  |  | N/X | 300 | 101 | 110.5 | 0.04 | 0.02 |
|  |  |  | 320 | 107 | 110.9 | 0.05 | 0.03 |
|  |  |  | 340 | 115 | 111.3 | 0.08 | 0.06 |
| 5 | a2(80) –b2(80) –c1(120) (Comparative example) | N | 290 300 | 83 87 | 105.2 hot spot | 0.08 | — |
| 6 | a1(80) –b1(80) –c3(120) (Comparative example) | N | 290 300 | 83 87 | 104.2 103.3 | 1.43 2.71 | — — |

EXAMPLE 2

A reactor tube with an inside diameter of 25 mm was immersed in a niter bath controlled at an optimum temperature (300 to 330° C.) and filled with the catalysts shown in Table 1 in the order of Catalyst C, Catalyst B and Catalyst A from the bottom upward and a gaseous mixture of acenaphthene and air was passed from the top of the reactor tube. The reaction conditions and the results are shown in Table 5.

TABLE 5

| Experi-ment No. | Catalyst (Length of layer: mm) | Raw material | GHSV hr⁻¹ | Concentration g/m³ | Yield wt % |
|---|---|---|---|---|---|
| 1 | a2(1000) – b1(1000) – c4(800) | ACN | 3000 | 100 | 118.5 |
| 2 | a3(1000) – b2(1000) – c1(800) | ACN | 3000 | 100 | 119.3 |
| 3 | a4(1400) – b4(1400) | ACN | 3000 | 100 | 120.5 |

(Notes) ACN = acenaphthene
Yield = yield of phthalic anhydride

EXAMPLE 3

A reactor tube with an inside diameter of 25 mm was immersed in a niter bath controlled at an optimum temperature (340 to 360° C.) and filled with the catalysts shown in Table 1 in the order of Catalyst C, Catalyst B and Catalyst A from the bottom upward and a gaseous mixture of indene or indane and air was passed from the top of the reactor tube. The reaction conditions and the results are shown in Table 6.

TABLE 6

| Experi-ment No. | Catalyst (Length of layer: mm) | Raw material | GHSV hr⁻¹ | Concentration g/m³ | Yield wt % |
|---|---|---|---|---|---|
| 1 | a3(1000) – b1(800) – c1(1000) | IDE IDA | 2900 2900 | 120 120 | 121.2 120.5 |
| 2 | a1(1000) – b2(800) – c1(1000) | IDE IDA | 2900 2900 | 120 120 | 120.6 119.8 |

(Notes) IDE = indene
IDA = indane
Yield = yield of phthalic anhydride

EXAMPLE 4

A reactor tube with an inside diameter of 25 mm was immersed in a niter bath controlled at an optimum temperature (360 to 380° C.) and filled with the catalysts shown in Table 1 in the order of Catalyst C, Catalyst B and Catalyst A from the bottom upward and a gaseous mixture of durene and air was passed from the top of the reactor tube. The reaction conditions and the results are shown in Table 7.

TABLE 7

| Experi-ment No. | Catalyst (Length of layer: mm) | Raw material | GHSV hr⁻¹ | Concentration g/m³ | Yield wt % |
|---|---|---|---|---|---|
| 1 | a3(1000) – b1(800) – c1(1000) | DUR | 3300 | 50 | 105.2 |
| 2 | a2(1000) – b3(800) – c4(1000) | DUR | 3300 | 50 | 106.2 |

(Notes) DUR = durene
Yield = yield of phthalic anhydride

EXAMPLE 5

A reactor tube with an inside diameter of 25 mm was immersed in a niter bath controlled at an optimum temperature (340 to 360° C.) and filled with the catalysts shown in Table 2 in the order of Catalyst C, Catalyst B and Catalyst A from the bottom upward and a gaseous mixture of naphthalene or ortho-xylene and air was passed from the top of the reactor tube. The reaction conditions and the results are shown in Tables 8 to 10.

Tables 8 to 10, the terms catalyst, length of layer in parentheses, N, S, and N/X in the raw material column, concentration, and PA, NQ and PL in the yield column are the same as those in Tables 3 and 4 above.

TABLE 8

| Experi-ment No. | Catalyst (Length of layer: mm) | Raw material | GHSV hr⁻¹ | Concentration g/m³ | Yield PA wt % | NQ wt % | PL wt % |
|---|---|---|---|---|---|---|---|
| 1 | A2(700) –B2(800) –C1(1500) | N X N/X | 2900 2800 2800 | 140 140 120 | 106.1 115.3 111.1 | 0.17 — 0.10 | — 0.10 0.03 |
| 2 | A4(700) –B1(800) –C1(1500) | N X N/X | 2900 2800 2800 | 140 140 120 | 106.3 114.9 111.0 | 0.21 — 0.15 | — 0.11 0.05 |

TABLE 8-continued

| Experiment No. | Catalyst (Length of layer: mm) | Raw material | GHSV hr$^{-1}$ | Concentration g/m$^3$ | Yield PA wt % | Yield NQ wt % | Yield PL wt % |
|---|---|---|---|---|---|---|---|
| 3 | A4(700) | N | 2900 | 140 | 106.0 | 0.08 | — |
|  | -B3(800) | X | 2800 | 140 | 115.1 | — | 0.07 |
|  | -C1(1500) | N/X | 2800 | 120 | 111.3 | 0.12 | 0.03 |
| 4 | A4(700) | N | 2900 | 140 | 106.2 | 0.13 | — |
|  | -B4(800) | X | 2800 | 140 | 115.0 | — | 0.11 |
|  | -C1(1500) | N/X | 2800 | 120 | 111.1 | 0.08 | 0.06 |
| 5 | A4(700) | N | 2900 | 140 | 106.0 | 0.10 | — |
|  | -B5(800) | X | 2800 | 140 | 115.3 | — | 0.10 |
|  | -C1(1300) | N/X | 2800 | 120 | 111.0 | 0.05 | 0.03 |
| 6 | A4(700) | N | 2900 | 140 | 106.3 | 0.10 | — |
|  | -B1(800) | X | 2800 | 140 | 115.2 | — | 0.10 |
|  | -C1(1300) | N/X | 2800 | 120 | 111.0 | 0.05 | 0.03 |
| 7 | A5(700) | N | 2900 | 140 | 106.1 | 0.12 | — |
|  | -B1(800) | X | 2800 | 140 | 114.9 | — | 0.11 |
|  | -C1(1300) | N/X | 2800 | 120 | 110.0 | 0.06 | 0.05 |
| 8 | A6(700) | N | 2900 | 140 | 106.3 | 0.15 | — |
|  | -B1(800) | X | 2800 | 140 | 115.1 | — | 0.14 |
|  | -C1(1300) | N/X | 2800 | 120 | 110.5 | 0.10 | 0.08 |
| 9 | A7(700) | N | 2900 | 140 | 106.0 | 0.05 | — |
|  | -B1(800) | X | 2800 | 140 | 115.0 | — | 0.04 |
|  | -C1(1300) | N/X | 2800 | 120 | 110.1 | 0.02 | 0.02 |
| 10 | A2(700) | N | 2900 | 140 | 105.9 | 0.02 | — |
|  | -B1(800) | X | 2800 | 140 | 114.7 | — | 0.03 |
|  | -C2(1500) | N/X | 2800 | 120 | 110.1 | 0.01 | 0.01 |
| 11 | A2(700) | N | 2900 | 140 | 106.3 | 0.22 | — |
|  | -B1(800) | X | 2800 | 140 | 115.1 | — | 0.13 |
|  | -C3(1500) | N/X | 2800 | 120 | 111.0 | 0.16 | 0.07 |

TABLE 9

| Experiment No. | Catalyst (Length of layer: mm) | Raw material | GHSV hr$^{-1}$ | Concentration g/m$^3$ | Yield PA wt % | Yield NQ wt % | Yield PL wt % |
|---|---|---|---|---|---|---|---|
| 12 | A2(700) | N | 2900 | 140 | 105.8 | 0.01 | — |
|  | -B1(800) | X | 2800 | 140 | 114.7 | — | 0.02 |
|  | -C4(1500) | N/X | 2800 | 120 | 110.1 | tr | 0.01 |
| 13 | A2(700) | N | 2900 | 140 | 106.1 | 0.12 | — |
|  | -B1(800) | X | 2800 | 140 | 115.2 | — | 0.05 |
|  | -C5(1500) | N/X | 2800 | 120 | 111.1 | 0.06 | 0.03 |
| 14 | A2(700) | N | 2900 | 140 | 106.0 | 0.12 | — |
|  | -B6(800) | X | 2800 | 140 | 115.2 | — | 0.06 |
|  | -C1(1300) | N/X | 2800 | 120 | 111.2 | 0.06 | 0.02 |
| 15 | A2(700) | N | 2900 | 140 | 105.9 | 0.05 | — |
|  | -B7(800) | X | 2800 | 140 | 114.9 | — | 0.04 |
|  | -C1(1300) | N/X | 2800 | 120 | 111.2 | 0.02 | 0.02 |
| 16 | A2(700) | N | 2900 | 140 | 106.2 | 0.15 | — |
|  | -B1(800) | X | 2800 | 140 | 115.3 | — | 0.07 |
|  | -C6(1300) | N/X | 2800 | 120 | 111.2 | 0.07 | 0.04 |
| 17 | A2(700) | N | 2900 | 140 | 106.3 | 0.13 | — |
|  | -B1(800) | X | 2800 | 140 | 114.8 | — | 0.07 |
|  | -C7(1300) | N/X | 2800 | 120 | 110.8 | 0.07 | 0.03 |
| 18 | A1(700) | N | 2900 | 140 | 106.0 | 0.18 | — |
|  | -B1(800) | X | 2800 | 140 | 115.1 | — | 0.12 |
|  | -C1(1300) | N/X | 2800 | 120 | 111.0 | 0.09 | 0.07 |
| 19 | A7(700) | N | 2900 | 140 | 105.9 | 0.02 | — |
|  | -B1(800) | X | 2800 | 140 | 114.7 | — | 0.03 |
|  | -C2(1500) | N/X | 2800 | 120 | 110.1 | 0.01 | 0.01 |
| 20 | A8(700) | N | 2900 | 140 | 106.3 | 0.22 | — |
|  | -B7(800) | X | 2800 | 140 | 115.1 | — | 0.13 |
|  | -C3(1500) | N/X | 2800 | 120 | 111.0 | 0.16 | 0.07 |
| 21 | A9(700) | N | 2900 | 140 | 105.8 | 0.01 | — |
|  | -B8(800) | X | 2800 | 140 | 114.7 | — | 0.02 |
|  | -C3(1500) | N/X | 2800 | 120 | 110.1 | tr | 0.01 |
| 22 | A10(700) | N | 2900 | 140 | 106.1 | 0.12 | — |
|  | -B9(800) | X | 2800 | 140 | 115.2 | — | 0.05 |
|  | -C3(1500) | N/X | 2800 | 120 | 111.1 | 0.06 | 0.03 |

TABLE 10

| Experiment No. | Catalyst (Length of layer: mm) | Raw material | GHSV hr$^{-1}$ | Concentration g/m$^3$ | Yield PA wt % | Yield NQ wt % | Yield PL wt % |
|---|---|---|---|---|---|---|---|
| 23 | A11(700) | N | 2900 | 140 | 106.0 | 0.12 | — |
|  | -B10(800) | X | 2800 | 140 | 115.2 | — | 0.06 |
|  | -C8(1500) | N/X | 2800 | 120 | 111.1 | 0.06 | 0.02 |
| 24 | A2(700) | N | 2900 | 140 | 105.9 | 0.05 | — |
|  | -B11(800) | X | 2800 | 140 | 114.9 | — | 0.04 |
|  | -C9(1500) | N/X | 2800 | 120 | 111.2 | 0.02 | 0.02 |
| 25 | A2(700) | N | 2900 | 140 | 106.2 | 0.15 | — |
|  | -B1(800) | X | 2800 | 140 | 115.3 | — | 0.07 |
|  | -C10(1500) | N/X | 2800 | 120 | 111.2 | 0.07 | 0.04 |
| 26 | A2(700) | N | 2900 | 140 | 106.3 | 0.13 | — |
|  | -B1(800) | X | 2800 | 140 | 114.8 | — | 0.07 |
|  | -C11(1500) | N/X | 2800 | 120 | 110.8 | 0.07 | 0.03 |
| 27 | A1(700) | N | 2900 | 140 | 106.0 | 0.18 | — |
|  | -B1(800) | X | 2800 | 140 | 115.1 | — | 0.12 |
|  | -C1(1500) | N/X | 2800 | 120 | 111.0 | 0.09 | 0.07 |
| 28 | A12(700) | N | 2900 | 110 | 106.0 | 0.01 | — |
|  | -B12(800) | X | 2900 | 110 | 115.0 | — | 0.01 |
|  | -C12(1300) | N/X | 2900 | 110 | 110.4 | 0.01 | — |
| 29 | A13(700) | N | 2900 | 110 | 106.2 | 0.01 | — |
|  | -B13(800) | X | 2900 | 110 | 115.3 | — | — |
|  | -C13(1300) | N/X | 2900 | 110 | 110.2 | 0.01 | — |
| 30 | A1(1400) | N | 2900 | 100 | 106.2 | 0.01 | — |
|  | -C1(1400) | X | 2900 | 110 | 115.2 | — | 0.01 |
|  |  | N/X | 2900 | 100 | 111.3 | 0.01 | — |
| 31 | A2(1400) | N | 2900 | 100 | 106.4 | 0.02 | — |
|  | -C1(1400) | X | 2900 | 110 | 115.6 | — | 0.01 |
|  |  | N/X | 2900 | 100 | 110.6 | 0.01 | 0.01 |
| 32 | A8(1400) | N | 2900 | 100 | 106.3 | 0.01 | — |
|  | -C4(1400) | X | 2900 | 110 | 115.4 | — | 0.01 |
|  |  | N/X | 2900 | 100 | 110.8 | 0.01 | 0.01 |
| 33 | A11(1400) | N | 2900 | 100 | 106.1 | 0.02 | — |
|  | -C8(1400) | X | 2900 | 110 | 115.0 | — | 0.01 |
|  |  | N/X | 2900 | 100 | 110.7 | 0.01 | 0.01 |

Comparative Example 2

The reaction was carried out by using the catalysts shown in Table 2 under the conditions shown in Table 11. The results are shown in Table 11.

In Table 11, the terms catalyst, length of layer in parentheses, N, X and N/X in the raw material column, concentration, and PA, NQ and PL in the yield column are the same as those in Tables 3 and 4 above.

TABLE 11

| Experiment No. | Catalyst (Length of layer: mm) | Raw material | GHSV hr$^{-1}$ | Concentration g/m$^3$ | Yield PA wt % | Yield NQ wt % | Yield PL wt % |
|---|---|---|---|---|---|---|---|
| 34 | A14(700) | N | 2900 | 120 | 102.0 | — | — |
|  | -B1(800) | X | 2900 | 140 | 108.1 | — | — |
|  | -C1(1300) | N/X | 2900 | 120 | 107.4 | — | — |
| 35 | A15(700) | N | 2900 | 120 | 104.0 | 2.31 | — |
|  | -B1(800) | X | 2900 | 120 | 107.2 | — | 1.2 |
|  | -C1(1300) |  |  |  |  |  |  |
| 36 | A16(700) | N | 2900 | 120 | 104.3 | — | — |
|  | -B1(800) | X | 2900 | 120 | 109.2 | — | — |
|  | -C1(1300) |  |  |  |  |  |  |
| 37 | A17(700) | N | 2900 | 120 | 104.2 | 1.53 | — |
|  | -B1(800) | X | 2900 | 120 | 108.5 | — | 1.0 |
|  | -C1(1300) |  |  |  |  |  |  |
| 38 | A18(700) | N | 2900 | 120 | 104.3 | 1.35 | — |
|  | -B1(800) | X | 2900 | 120 | 109.5 | — | 0.8 |
|  | -C1(1300) |  |  |  |  |  |  |
| 39 | A1(700) | N | 2900 | 120 | 104.0 | — | — |
|  | -B14(800) | X | 2900 | 120 | 109.3 | — | — |
|  | -C1(1300) |  |  |  |  |  |  |

TABLE 11-continued

| Experiment No. | Catalyst (Length of layer: mm) | Raw material | GHSV hr$^{-1}$ | Concentration g/m³ | Yield PA wt % | NQ wt % | PL wt % |
|---|---|---|---|---|---|---|---|
| 40 | A1(700)–B15(800)–C1(1300) | N<br>X | 2900<br>2900 | 120<br>120 | 103.8<br>107.3 | 2.53<br>— | —<br>1.64 |
| 41 | A1(700)–B1(800)–C14(1300) | N<br>X | 2900<br>2900 | 120<br>120 | 104.8<br>108.5 | 1.41<br>— | —<br>1.32 |
| 42 | A1(700)–B1(800)–C15(1300) | N<br>X | 2900<br>2900 | 120<br>120 | 103.5<br>106.5 | 2.33<br>— | —<br>1.85 |

INDUSTRIAL APPLICABILITY

According to this invention, hydrocarbons such as naphthalene, xylene, benzene, toluene, durene, butene, acenaphthene, anthracene, indene and their derivatives can be oxidized in vapor phase in high yields with high productivity. Moreover, naphthalene or xylene can be oxidized in vapor phase to phthalic anhydride in high yields with high productivity.

What is claimed is:

1. A process for vapor-phase oxidation of hydrocarbons which may contain substituents by passing a gaseous mixture comprising of a molecular oxygen-containing gas and said hydrocarbons to a fixed bed of catalyst layers which comprises passing said gaseous mixture to a fixed bed of catalyst layers wherein the void ratio of the catalyst layers increases by stages in one step or more from upstream downward in the flow of said gaseous mixture.

2. A process for vapor-phase oxidation as described in claim 1 wherein the void ratio $V_1$ of the most upstream catalyst layer and the void ratio $V_2$ of the most downstream catalyst layer satisfy the relationship $V_1/V_2 = 0.6$–$0.9$.

3. A process for vapor-phase oxidation as described in claim 1 or 2 wherein the oxidative activity of the catalysts constituting the catalyst layers increases by stages in one step or more from upstream downward.

4. A process for vapor-phase oxidation as described in claim 1 wherein said hydrocarbons are naphthalene and/or ortho-xylene and the oxidation reaction product is phthalic anhydride.

5. A process for preparing phthalic anhydride by passing a gaseous mixture comprising of a molecular oxygen-containing gas and naphthalene and/or ortho-xylene to a fixed bed of catalyst layers which comprises using catalysts containing titanium dioxide and vanadium pentoxide as catalytically active components and passing said gaseous mixture to a fixed bed of catalyst layers wherein the void ratio of the catalyst layers increases by stages in one step or more from upstream downward in the flow of said gaseous mixture.

6. A process for preparing phthalic anhydride as described in claim 5 wherein the oxidative activity of the catalysts constituting the catalyst layers increases by stages in one step or more from upstream downward.

7. A process for preparing phthalic anhydride as described in claim 5 or 6 wherein a gaseous mixture comprising of naphthalene and/or ortho-xylene and a molecular oxygen-containing gas is oxidized by contact with a layer of upstream catalyst comprising a catalyst placed upstream in the flow of said gaseous mixture and a layer of downstream catalyst comprising a catalyst placed downstream in the flow of said gaseous mixture, said upstream catalyst being made by depositing catalytically active components containing 75 to 90% by weight of titanium dioxide, 10 to 20% by weight of vanadium pentoxide, 1.0 to 3.5% by weight of a compound of cesium (calculated as sulfate) and 0.1 to 1.0% by weight of a compound of at least one metal selected from barium, magnesium, yttrium, lanthanum and cerium (calculated as oxide of selected metal) and showing a specific surface area of 100 to 160 m²/g on a nonporous inert carrier and said downstream catalyst being made by depositing catalytically active components containing less than 0.1% by weight of a compound of alkali metal (calculated as sulfate), 75 to 90% by weight of titanium dioxide, 10 to 20% by weight of vanadium pentoxide, 1.0 to 3.0% by weight of a compound of phosphorus (calculated as oxide) and 0.3 to 2.0% by weight of a compound of at least one metal selected from tungsten, molybdenum, tin, antimony and bismuth (calculated as oxide of selected metal) and showing a specific surface area of 70 to 100 m²/g on a nonporous inert carrier.

8. A process for preparing phthalic anhydride as described in claim 7 wherein said upstream catalyst layer is composed of two kinds or more of catalyst layers with the amount of said compound of cesium increasing by stages toward upstream and the catalyst layer placed most upstream contains 1.5 to 3.5% by weight of said compound of cesium (calculated as sulfate) and 0.3 to 1.8% by weight of said compound of at least one metal selected from barium, magnesium, yttrium, lanthanum and cerium (calculated as oxide of selected metal) and shows a specific surface area of 100 to 140 m²/g while the catalyst layer placed most downstream in the upstream layer contains 1.0 to 2.0% by weight of said compound of cesium (calculated as sulfate) and 0.1 to 1.6% by weight of said compound of at least one metal selected from barium, magnesium, yttrium, lanthanum and cerium (calculated as oxide of selected metal) and shows a specific surface area of 120 to 160 m²/g.

9. A process for vapor-phase oxidation as described in claim 1, wherein the void ratio of catalyst layers is changed in at least two steps.

10. A process for vapor-phase oxidation as described in claim 1, wherein the void ratio of catalyst layers is changed in 2–3 steps.

11. A process for vapor-phase oxidation as described in claim 9, wherein the void ratio of catalyst layers is changed in at least 3 layers of catalyst.

12. A process for vapor-phase oxidation as described in claim 9, wherein the difference in void ratio between the adjacent catalyst layers is 5 to 25%.

13. A process for vapor-phase oxidation as described in claim 12, wherein the difference in void ratio between the adjacent catalyst layers is 8 to 16%.

14. A process for vapor-phase oxidation as described in claim 2, wherein $(V_1)/(V_2)$ is 0.7–0.8.

* * * * *